United States Patent
Stocker et al.

(12) 
(10) Patent No.: US 6,486,154 B1
(45) Date of Patent: Nov. 26, 2002

(54) (HETERO) ARYL-SULFONAMIDE DERIVATIVES, THEIR PREPARATION AND THEIR USE AS FACTOR XA INHIBITORS

(75) Inventors: Andrew Stocker; John Preston, both of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/463,446

(22) PCT Filed: Jul. 23, 1998

(86) PCT No.: PCT/GB98/02200

§ 371 (c)(1),
(2), (4) Date: Jan. 27, 2000

(87) PCT Pub. No.: WO99/09027

PCT Pub. Date: Feb. 25, 1999

(30) Foreign Application Priority Data

Jul. 29, 1997 (GB) ............................................. 9715895

(51) Int. Cl.[7] ........................ A61K 31/54; A61K 31/535; C07D 403/00; C07D 413/00; C07D 260/30

(52) U.S. Cl. .............................. 514/231.5; 514/227.8; 544/295; 544/106; 544/111; 544/1

(58) Field of Search ........................... 514/227.8, 231.5; 544/106, 111, 295

(56) References Cited

U.S. PATENT DOCUMENTS

| | | | |
|---|---|---|---|
| 4,167,567 A | 9/1979 | McCall | 424/250 |
| 4,231,938 A | 11/1980 | Monaghan et al. | 260/343.5 |
| 4,537,896 A | 8/1985 | Claeson et al. | 514/330 |
| 4,564,610 A | 1/1986 | Rahtz et al. | 514/80 |
| 4,629,728 A | 12/1986 | Regnier et al. | 514/252 |
| 4,788,196 A | 11/1988 | Cross et al. | 514/252 |
| 4,806,536 A | 2/1989 | Cross et al. | 514/252 |
| 4,835,165 A | 5/1989 | Cross et al. | 514/318 |
| 4,840,963 A | 6/1989 | Shepard et al. | 514/418 |
| 4,968,704 A | 11/1990 | Cross et al. | 514/318 |
| 5,032,604 A | 7/1991 | Baldwin et al. | 514/361 |
| 5,138,058 A | 8/1992 | Geisen et al. | 544/295 |
| 5,254,563 A | 10/1993 | Huth et al. | 514/292 |
| 5,332,822 A | 7/1994 | Misra | 546/164 |
| 5,364,865 A | 11/1994 | Diana | 514/318 |
| 5,371,091 A | 12/1994 | Misra et al. | 514/314 |
| 5,391,556 A | 2/1995 | Heckel et al. | 514/322 |
| 5,411,971 A | 5/1995 | Emonds-Alt et al. | 514/318 |
| 5,556,977 A | 9/1996 | Wayne et al. | 544/380 |
| 5,563,141 A | 10/1996 | Wayne et al. | 514/252 |
| 5,580,881 A | 12/1996 | Binet et al. | 514/307 |
| 5,606,065 A | 2/1997 | Emonds-Alt et al. | 546/223 |
| 5,681,954 A | 10/1997 | Yamamoto et al. | 544/114 |
| 5,795,893 A | 8/1998 | Bondinell et al. | 514/252 |
| 5,856,326 A | 1/1999 | Anthony et al. | 514/252 |
| 5,883,096 A | 3/1999 | Lowe et al. | 514/252 |
| 5,908,843 A | 6/1999 | Gante et al. | 514/255 |
| 6,022,869 A | 2/2000 | Faull | 514/227.8 |
| 6,037,343 A | 3/2000 | Ali | 514/252 |

FOREIGN PATENT DOCUMENTS

| | | |
|---|---|---|
| AU | 10177/92 | 7/1992 |
| DE | 39 05 364 A1 | 8/1990 |
| DE | 39 43 225 A | 6/1991 |
| DE | 42 43 858 A1 | 6/1994 |
| DE | 43 06 506 A1 | 9/1994 |
| EP | 0 097 630 A2 | 1/1984 |
| EP | 0 232 740 A1 | 8/1987 |
| EP | 0 233 051 | 8/1987 |
| EP | 0 244 115 | 11/1987 |

(List continued on next page.)

OTHER PUBLICATIONS

Zaoral M. & Sorm F.: "Amino acids and peptides. LIX. Synthesis and some biological properties of L–DABB–vasopressin" Collect. Czech. Chem. Commun., vol. 31, 1966, pp. 90–95, XP002081879 see compound II, p. 95.

(List continued on next page.)

*Primary Examiner*—Mukund J. Shah
*Assistant Examiner*—Sudhaker B. Patel
(74) *Attorney, Agent, or Firm*—Morgan, Lewis & Bockius LLP

(57) ABSTRACT

A compound of formula (I),

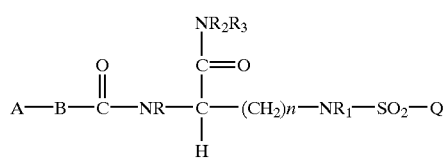

or a pharmaceutically-acceptable salt thereof, wherein A is an optionally substituted 5- or 6-membered monocyclic aromatic ring containing 1, 2 or 3 ring heteroatoms; B is optionally substituted phenylene or a 6-membered heterocyclic ring containing 1, 2 or 3 nitrogen heteroatoms; R and $R_1$ are hydrogen or (1–4C)alkyl; n is 1 or 2; $R_2$ and $R_3$ are hydrogen, (1–6C)alkyl, (4–7C)cycloalkyl, or (2–6C) alkenyl, or $R_2$ and $R_3$ may form along with the nitrogen to which they are attached a 5-, 6- or 7-membered heterocyclic ring, wherein each $R_2$ or $R_3$ group or any heterocyclic ring formed from $R_2$ and $R_3$ may be optionally substituted with various substituent groups, and wherein Q may be optionally substituted by various substituent groups, which possesses antithrombotic and anticoagulant properties and are accordingly useful in methods of treatment of humans or animals. The invention relates to processes for the preparation of the compounds represented by formula (I), to pharmaceutical compositions containing them, and to their use in the manufacture of medicaments for use in the production of an antithrombotic or anticoagulant effect.

10 Claims, No Drawings

FOREIGN PATENT DOCUMENTS

| | | |
|---|---|---|
| EP | 0 324 421 A2 | 7/1989 |
| EP | 0 308 337 | 8/1989 |
| EP | 0 352 946 A1 | 1/1990 |
| EP | 0 359 389 | 3/1990 |
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 555 824 A1 | 8/1993 |
| EP | 0 576 941 A1 | 1/1994 |
| EP | 0 608 759 A2 | 8/1994 |
| FR | 2 697 252 A1 | 4/1994 |
| GB | 1 449 100 | 7/1976 |
| IE | 920095 | 7/1992 |
| WO | WO 92/08709 | 5/1992 |
| WO | WO 92/18478 | 10/1992 |
| WO | WO 93/06085 | 4/1993 |
| WO | WO 94/18185 | 8/1994 |
| WO | WO 94/20467 | 9/1994 |
| WO | WO 94/20468 | 9/1994 |
| WO | WO 94/22835 | 10/1994 |
| WO | WO 96/05189 | 2/1996 |
| WO | 9610022 * | 4/1996 |
| WO | 96100022 * | 4/1996 |
| WO | WO 96/26196 | 8/1996 |
| WO | WO 96/30343 | 10/1996 |
| WO | WO 96/33171 | 10/1996 |
| WO | WO 97/06802 | 2/1997 |
| WO | WO 97/21829 | 8/1997 |
| WO | WO 97/28128 | 8/1997 |
| WO | WO 97/29104 | 8/1997 |
| WO | 97/29104 A | 8/1997 |
| WO | WO 97/30971 | 8/1997 |
| WO | WO 98/06705 | 2/1998 |
| WO | WO 98/21188 | 5/1998 |

OTHER PUBLICATIONS

Boissier et al., "Synthesis and Pharmacological Study of New Piperazine Derivatives. I. Benzylpiperazines", J. Med. Chem., Sep. 1963, pp. 541–544.

Conway et al., "Approaches to the Generation of 2,3–Indolyne"; Heterocycles, 1992, 34(11) 2095–2108.

Deratani et al., "Synthesis of new dialkylaminopyridine acylation catalysts and their attachment ot insoluble polymer supports", Polymer, Apr. 1987, pp. 825–830.

Hibino et al.; "N–Phenysulfonylindole derivatives", Chemical Abstracts, 118:147461, Apr. 1993.

Jain et al., "Compounds Acting on the Central Nervous System, VII. Studies in 1–Pyridyl–1–substituted Piperazines. A New Class of Anticonvulsants", J. Med. Chem., Sep. 1967, pp. 812–818.

Kataoka et al., Chemical Abstracts, vol. 123, No. 14, Oct. 2, 1995 Columbus, Ohio, US; abstract No. 179521d, "Homopiperazines as cell migration inhibitors." Xp002081582 see abstract & JP 95 145060 A (TEJIN LTD).

Prasad et al., "Antiamoebic Action of Drugs and Synthetic Compounds Against Trophozoites of Entamoeba Histolytica Under Axenic and Polyxenic Culture Conditions and in the Infected Rat Caecum", Curr. Sci., Aug. 1984, pp. 778–781.

Caulkett et al., Chemical Abstracts, vol. 131:322629.

Kobayashi et al., Chemical Abstracts, vol. 130:296694.

Kobayashi et al., Chemical Abstracts, vol. 132:194391.

Nowak et al., Chemical Abstracts, vol. 131:337034.

Take et al., Chemical Abstracts, vol. 133:58814.

Tawada et al., Chemical Abstracts, vol. 130:38404.

Tawada et al., Chemical Abstracts, vol. 131:170361.

Ratouis et al., "Synthesis and pharmacological Study of New Piperazine Derivatives, II. Phenethylpiperazines", J. Med. Chem., Jan. 1965, pp. 104–107.

Sato et al., "Synthetic Studies on Cardiovascular Agents. III. Synthesis of Pyrano–[2,3–c]pyrazoline Derivatives", Yakugaku Zasshi, vol. 98(3), 1978, pp. 335–348.

Saxena et al., "Quantitative Structure Activity Relationship in 3–4 Disubstituted Pyridines & I–(3"–Amino–4"–pyridyl)–4–arylpiperazines" Indian J. Chem. vol. 19B, Oct. 1980, pp. 873–878.

Sundberg et al. "Synthesis with N–Protected 2–Lithioindoles"; J. Org. Chem., 1973 38(19) 3324–3330.

Von G. Krüger, et al.; (Thomae et al.) Arzneim.–Fosch., Synthesen von N–Benzyl–aminocarbonsäuren und thren Derivaten; (Synthesis and N–benzylaminocarboxylic acids and their derivatives), vol. 23(2a), pp. 290–295.

Yokoyama et al. "Palladium–catalyzed cross–coupling reaction: direct allylation of aryl bromides with allyl acetate" Tetrahedron Letters., vol. 26, No. 52—1985 pp. 6457–6460, XP002081581 Oxford GB * p. 6458–6459: compound 7.

Bowers Nemia et al., "Synthetic Routes to 3–Pyrrolidinol", Synth. Comm., 13(13):1117–1123 (1983).

Budavari: Merck Index, vol. 11 ED., 1989, See Monograph Nos. 804 and 2807.

Cattel et al: "Drug design based on biosynthetic studies: synthesis, biological activity, and kinetics of new inhibitors of 2,3–oxidosualene cyclase and squalene epoxidase.", Steroids., vol. 53, No. 3–5, 1989, pp. 363–391, XP000611661.

Chambers et al "Preparation of arylpyridine compounds for treating leukotriene–related diseases", Chemical Abstracts, Astract No. 139113, vol. 119 (1993).

Cross et al., "Preparation of N–[(heterocyclicylmethoyx) phenyl]sulfamides and analogs as antiarrhythmics", Chemical Abstracts, Abstract No. 231211, vol. 113 (1989).

E. Jucker, "Über C–substituierte Piperazinderativate", Helv. Chim. Acta., 45:2383–2042 (1962).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. [1]) Reactions of Acetoacetamide and β–Aminocrotonamide with β–Diketone, β—Ketoaldehyde and Related Compounds", Chem. Pharm. Bull., 24(2):303–309 (1976).

Kettner et al., "The Selective Inhibition of Thrombin by Peptides of Boroarginine", The Journal of Biological Chemistry, vol. 265, No. 30, pp. 18289–18297 (1990).

Mitsunobu et al., "Preparation of Carboxylic Esters and Phosphoric Esters by the Activation of Alcohols", Bull. Chem. Soc. Jpn., 44(12):3427–3430 (1971).

Sartori et al., "Synthesis and analgesic activities of urea derivatives of α–amino–N–pyridyl benzene propanamide", Eur J. Med Chem (1994), 431–439.

Smith et al., "Fibrin, Red Cell and Platelet Interactions in an Experimental Model of Thrombosis", Br. J. Pharmac., vol. 77, pp. 29–38 (1982).

Szmant et al., "Concerning the Variable Character of the Sulfone Group", J. Amer. Chem. Soc., vol. 78, pp. 3400–3403 (1956).

Tabacik et al: "Squalene expoxidase, oxido–squalene cyclase and cholesterol biosynthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

Vigroux et al., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Produrgs of Acetamiophen", J. Med. Chem., vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Wallis, "Inhibitors of Coagulation Factor Xa: From Macromolecular Beginnings to Small Molecules", Current Opinion in Therapeutic Patents, Aug., 1993, pp. 1173–1179.

Zoral et al., "Amino acids and peptides. LIX. Synthesis and some biological properties of L–DABB–vasopressin", Collect. Czech. Chem. Commun., vol. 31, 1966, pp. 90–95, XPOO2081879 see compound 11, p. 95.

E. Jucker, "Über C–substituiterte Piperazinderativate", Helv. Chim. Acta., 45:2383–2042 (1962).

* cited by examiner

(HETERO) ARYL-SULFONAMIDE DERIVATIVES, THEIR PREPARATION AND THEIR USE AS FACTOR XA INHIBITORS

The invention relates to heterocyclic derivatives, or pharmaceutically-acceptable salts thereof, which possess antithirombotic and anticoagulant properties and are accordingly useful in methods of treatment of humans or animals. The invention also relates to processes for the preparation of the heterocyclic derivatives, to pharmaceutical composition containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis. *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenlyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism pulmonary embolism, isehaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

Accordingly in one aspect the present invention provides compounds of formula I

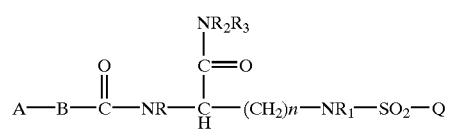

wherein:

A is an optionally substituted 5- or 6-membered monocyclic aromatic ring containing 1, 2 or 3 ring heteroatoms selected from oxygen, nitrogen and sulphur;

B is optionally substituted phenylene or a 6-membered heterocyclic ring containing 1, 2 or 3 nitrogen heteroatoms.

R and $R_1$ are independently selected from hydrogen and (1–4C)alkyl, n is 1 or 2;

$R_2$ and $R_3$ are independently selected from hydrogen, (1–6C)alkyl (4–7C)cycloalkyl, (2–6C)alkenyl on $R_2$ and $R_3$ may form along with the nitrogen to which they are attached a 5-, 6- or 7-membered heterocyclic ring which ma)y contain in addition to the nitrogen atom present 1 or 2 additional heteroatoms selected from nitrogen, oxygen and sulphur, wherein each $R_2$ or $R_3$ group or any heterocyclic ring formed from $R_2$ and $R_3$ may he optionally substituted by hydroxy, amino, carboxy, (1–4C)alkoxycarbonyl, oxo. (1–4)alkyl, hydroxy-(1–4C)alkyl, (1–4C)alkoxy-(1–4C)alkyl, carboxy-(1–4C)alkyl, (1–4C)alkoxycarbonyl-(1–4C) alkyl, or carbamoyl-(1–4C)alkyl;

Q is selected from phenyl, naphthyl, phenyl(1–4C)alkyl, phenyl(2–4C)alkenyl and a 5-, 6- or 7-membered heterocyclic ring containing up to 4 heteroatoms selected from nitrogen, oxygen and sulphur wherein Q may be optionally substituted by halo, halo(1–4C)alkyl, cyano, amino, hydroxy, carbamoyl, (1–4C)alkyl, (2–4C) alkenyl, (2–4C)alkynyl, (1–4C)alkoxy, (2–4C) alkenyloxy, (2–4C)alkynyloxy, (1–4C)alkylthio, (1–4C)alkylsulphilnyl, (1–4C)alkylsulphonyl, (1–4C) alkylamino, di(1–4C)alkylamino, (1–4C) alkoxycarbonyl, N-(1–4C)alkylcarbonoyl, (2–6C) alkanoyl, (2–4C)alkanoylamino, hydroxy-(1–4C)alkyl, (1–4C)alkoxy-(1–4C)alkyl, carboxy-(1–4C)alkyl. (1–4C)alkoxycarbonyl-(1–4C)alkyl, carbamoyl-(1–4C)alkyl, N-(1–4C)alkylcarbamoyl-(1–4C)alkyl, N,N-di(1–4C)alkylcarbamoyl-(1–4C)alkyl, phenyl, phenoxy, phenylthio, phenylsulphinyl, phenylsulphonyl, benzyl, benzoyl wherein said phenyl, phenoxy, phenylthio, phenylsulphinyl, phenylsulphonyl, benzyl or benzoyl substituent bears 1, 2 or 3 substituents selected from halo, trifluoromethyl, cyano, hydroxy, amino, nitro, carboxy, carbamoyl, (1–4C)alkyl, (1–4C)alkoxy, (1–4C)alkylamino, di(1–4C)alkylamino. (1–4C)alkoxycarbonyl, N,-(1–4C)alkylcarbamoyl, N,N,(1–4C)alkylcarbamoyl and (2–4C)alkanoylamino, or a pharmaceutically acceptable salt thereof.

In this specification the term "alkyl" includes both straight and branched chain alkyl groups but references to individual alkyl groups such as "propyl" are specific for the straight chain version only. An analogous convention applies to other generic terms.

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

Preferably A is a pyridyl, pyrimidinyl or pyridazinyl ring for example 4-pyridyl, 2-pyridyl, 4-pyridazinyl, 3-pyrimidinyl, 4-pyrimidinyl or 3-pyridyl. Of these 4-pyrimidinyl and 4-pyridyl are most preferred.

In one aspect A is unsubstituted. In another aspect A is substituted by one, two or three atoms or groups selected from halo (for example fluoro, chloro or bromo), oxo, carboxy, trifluoromethyl, cyano, amino, hydroxy, nitro, (1–4C)alkyl (for example methyl or ethyl), (1–4C)alkoxy (for example methoxy or ethoxy), (1–4C)alkoxycarbonyl (1–4C)alkylamino (for example methylamino or ethylamino) or di-(1–4C)alkylamino (for example dimethylamino or diethylamino). For the avoidance of doubt substituents on A may also be present, where possible, on the heteroatom of the ring. Preferred substituents of A are halo, (1–4C)alkyl, amino and (1–4C)alkylamino.

There are three preferred aspects of ring B:

1. In one aspect B is an optionally substituted 1,4-phenylene ring
2. In one aspect B is an optionally substituted 1,4-piperidinediyl ring, wherein A or the carbonyl group (—CO—) on either side of B is attached to the nitrogen atom of the ring or B is an optionally substituted 1,4-piperazinediyl ring, wherein both A and the carbonyl group (—CO—) on either side of B are attached to the nitrogen atoms atoms of the ring.
3. In one aspect B is a heterocyclic ring in which neither A nor the carbonyl group (—CO—) on either side of B are not attached to nitrogen atom(s) of B.

In a preferred aspect heterocyclic rings formed from $R_2$ and $R_3$ include 1-piperidino, 1-piperazinyl, 4-morpholino, 4-thiomorpholino, 1-imidazolidinyl and 1-pyrrolidinyl; preferred substitutions include oxo, hydroxy, amino and carboxy and include substitutions on any of the additional heteroatoms, for example 1-oxo-4-thiomorpholino and 1,1-dioxo-4-thiomorpholino.

In a preferred aspect R and $R_1$ are both hydrogen.

A suitable value for Q when it is naphthyl is, for example, 1-naphthyl or 2-naphthyl, when it is phenyl-(1–4C)alkyl is, for example, benzyl, phelnylethyl and 3-phelnylpropyl, when it is phenyl-(2–4C)alkenyl is, for example, styryl, cinnamyl or 3-phenylprop-2-enyl: and when it is phenyl-(2–4C)alkynyl is, for example, 2-phenylethynyl, 3-phenylprop-2-ynyl and 3-phenylprop-1-ynyl.

A suitable value for Q when it is a heterocyclic moiety containing up to 4 heteroatoms selected from nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quiniazolinyl, cinnolinyl, pyrrolyl, pyrrolidinyl, indolyl, indolinyl, imidazolyl, benzimildazolyl, pyrazolyl, indazolyl, oxazolyl, benzoxazolyl, isoxazolyl, thiazolyl, benzothilazolyl, isothiazolyl, morpholinol, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate $X_2$ group such as, for example, $SO_2$, $C(R^5)_2$ or CO, through any available nitrogen atom and which may bear up to three substituents including a substituent on any available nitrogen atom.

A suitable value for the heteroaryl substituent on Q or the heteroaryl group in a heteroaryl-containing substituent on Q which comprises a 5- or 6-membered monocyclic heteroaryl ring containing up to 3 heteroatoms selected from oxygen, nitrogen and sulphur is, for example, furyl, thienyl, pyridyl, pyrazinyl, pyrimidinyl, pyridazinyl, pyrrolyl, imidazolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including, through any available nitrogen atom.

Particularly preferred substituents of Q are selected from halo (ideally chloro or bromo) and $C_{1-4}$alkyl (ideally methyl).

Suitable values for optional substituents for B, Q and for $R_2$ and $R_1$ are:

| | |
|---|---|
| for (1-4C)alkyl: | methyl ethyl and propyl; |
| for (1-4C)alkoxycarbonyl | methoxycarbonyl, ethoxycarbonyl, propoxycarbonyl and tert-butoxycarbonyl; |
| for hydroxy-(1-4C)alkyl: | hydroxymethyl, 1-hydroxyethyl, 2-hydroxyethyl and 3-hydroxypropyl; |
| for (1-4C)alkoxy-(1-4C)alkyl: | methoxymethyl, ethoxymethyl, 1-methoxymethyl, 2-methoxyethyl, 2-ethoxyethyl and 3-methoxypropyl; |
| for carboxy-(1-4C)alkyl: | carboxymethyl, 1-carboxyethyl, 2-carboxyethyl and 3-carboxypropyl; |
| for (1-4C)alkoxycarbonyl-(1-4C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |

| | -continued |
|---|---|
| for carbamoyl-(1-4C)alkyl | carbamoylmethyl, 1-carbamoylethyl, 2-carbamoylethyl and 3-carbamoylpropyl; |

Suitable values for substituents (where applicable) which may be present on B, on a heterocyclic or phenyl group within a substituent on Ar, on Q or on a phenyl- or heteroaryl-containing substituent on Q include, for example:

| | |
|---|---|
| for halo: | fluoro, chloro, bromo; |
| for (1-4C)alkyl: | methyl, ethyl, propyl, butyl; |
| for (1-4C)alkoxy: | methoxy, ethoxy; |
| for (1-4C)alkylamino: | methylamino, ethylamino; |
| for di-(1-4C)alkylamino: | dimethylamino, diethylamino; |
| for (2-4C)alkenyl: | vinyl and allyl; |
| for (2-4C)alkynyl: | ethynyl and prop-2-ynyl; |
| for (2-4C)alkenyloxy: | vinyloxy and allyloxy; |
| for (2-4C)alkynyloxy: | ethynyloxy and prop-2-ynyloxy; |
| for 4-(1-4C)alkylpiperazin-1-yl: | 4-methylpiperazin-1-yl and 4-ethylpiperazin-1-yl; |
| for (1-4C)alkylthio: | methylthio, ethylthio and propylthio; |
| for (1-4C)alkylsulphinyl: | methylsulphinyl, ethylsulphinyl and propylsulphinyl; |
| for (1-4C)alkylsulphonyl: | methylsulphonyl, ethylsulphonyl and propylsulphonyl; |
| for (2-4C)alkanoylamino: | acetamido, propionamido and butyramido; |
| for (1-4C)alkanesulphonamido: | methanesulphonamido and ethanesulphonamido; |
| for (1-4C)alkoxycarbonyl: | methoxycarbonyl, ethoxycarbonyl, propoxycarbonyl and tert-butoxycarbonyl; |
| for N-(1-4C)alkylcarbamoyl: | N-methylcarbamoyl, N-ethylcarbamoyl and N-propylcarbamoyl; |
| for N,N-di-[(1-4C)alkyl]carbamoyl: | N,N-dimethylcarbamoyl, N-ethyl-N-methylcarbamoyl and N,N-diethylcarbamoyl; |
| for 4-(1-4C)alkylpiperazin-1-ylcarbonyl: | 4-methylpiperazin-1-ylcarbonyl and 4-ethylpiperazin-1-ylcarbonyl: |
| for (1-4C)alkanesulphonamidocarbonyl: | methanesulphonamidocarbonyl and ethanesulphonamidocarbonyl; |
| for (2-4C)alkanoyl: | acetyl propionyl and butyryl: |
| for hydroxy-(1-4C)alkyl: | hydroxymethyl, 1-hydroxyethyl, 2-hydroxyethyl and 3-hydroxypropyl: |
| for (1-4C)alkoxy-(1-4C)alkyl: | methoxymethyl, ethoxymethyl, 1-methoxymethyl, 2-methoxyethyl, 2-ethoxyethyl and 3-methoxypropyl; |
| for carboxy-(1-4C)alkyl: | carboxymethyl, 1-carboxyethyl, 2-carboxyethyl and 3-carboxypropyl; |
| for (1-4C)alkoxycarbonyl-(1-4C)alkyl: | methoxycarbonylmethyl, ethoxycarbonylmethyl, tert-butoxy-carbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1-4C)alkyl: | carbamoylmethyl, 1-carbamoylethyl, 2-carbamoylethyl and 3-carbamoylpropyl; |
| for N-(1-4C)alkylcarbamoyl-(1-4C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1-4C)alkyl]carbamoyl-(1-4C)alkyl: | N,N-dimethylcarbamoylmethyl, N-ethyl-N-methylcarbamoylmethyl N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |

A preferred class of compounds of the present invention is that wherein:

A is pyridyl, pyrimidinyl or pyridazinyl;

B is 1,4-piperidinediyl, 1,4-piperazinediyl or para-phenylene;

$R_2$ and $R_3$ are joined together to form a 6-membered heterocyclic ring, preferably substituted:

Q is styryl or naphthyl optionally substituted by fluoro, chloro or bromo or is phenyl optionally substituted by fluoro, chloro or bromo;

and pharmaceutically-acceptable salts thereof.

Particular compounds of the invention are those listed as Examples below.

A heterocyclic derivative of formula I, or pharmaceutically-acceptable salt thereof, may be prepared by any process known to be applicable to the preparation of related compounds. Such procedures are provided as a further feature of the invention and are illustrated by the following representative processes in which, unless otherwise stated A, B, $X_1$, R, $R_1$, $R_2$, $R_3$ and Q have any of the meanings defined hereinbefore wherein any functional group, for example amino, alkylamino, carboxy or hydroxy, is optionally protected by a protecting group which may be removed when necessary.

Compounds of formula I may be prepared by:

(a) Reacting an acid of formula (II) or a reactive derivative thereof.

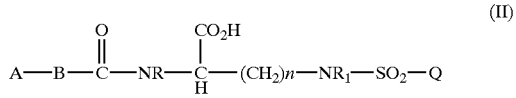
(II)

with an amine of formula $R_2R_3NH$ (III)

A suitable reactive derivative of an acid of the formula (III) is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated amide such as 1,1-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide, an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide, or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5,4,0]undec-7-ene.

The reaction is also preferably carried out in a suitable inert solvent or diluent, for example methylenle chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) Reacting an acid of formula (IV), or a reactive derivative thereof,

(IV)

with an amine of formula (V)

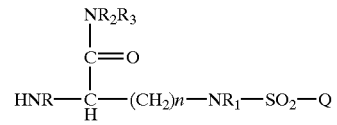
(V)

Suitable reactive derivatives of an acid of the formula (IV) and conditions are described in process method (a) above.

(c) Coupling a compound of formula (VI)

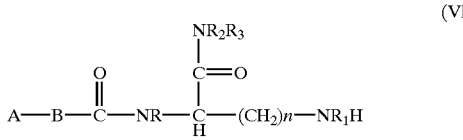

with a compound of formula $$Z-SO_2-Q \quad (VII)$$

wherein Z is a displaceable group such as halo, in conditions similar to those described in process method (a) above.

(d) For compounds of formula I, wherein A is attached to B by an alkyl bond, by coupling a compound of formula (VIII)

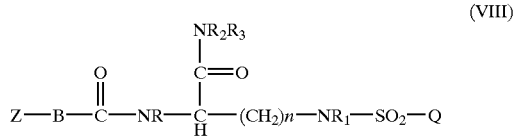

wherein Z is a displaceable group such as halo, with an activated derivative of heterocyclic ring A. Suitable activated derivatives include metalised derivatives such as with zinc or tin and borane derivatives. The activated derivative of heterocyclic ring A is reacted with a compound of formula (VII) to effect cross coupling where Z is a halo group, such as iodo. bromo or chloro, or triflate. Suitably the reaction is catalysed by use of a transition state metal catalyst, such as palladium, e.g. tetrakis (triphenylphosphine) palladium (0).

Alternatively it is possible that ring A contains the displaceable group Z and ring B is activated and the reaction performed as described above.

(e) For compounds of formula I, wherein A is attached to B by an alkyl bond, by forming A ring on compounds of formula (VIII), wherein Z is a functional group capable of cyclisation. Suitable reagents and conditions are described below in the preparation of compounds of formula (IV) by cyclisation.

(f) For compounds of formula I, wherein A is attached to B by an amide bond, by reacting an amine of formula (VIII), wherein Z is hydrogen, with a derivative of heterocyclic ring A containing a suitable displaceable group, such as halo, in the presence of a base in conditions similar to those described in process method (a) above.

(g) Oxidation of a compound of formula (IX)

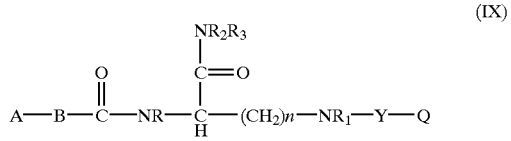

wherein Y is S or SO.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. Those compounds of formula (IX) which contain oxygen labile groups (such as A ring is pyridyl) are probably not suitable intermediates for this process step, unless oxidation of such groups is desired.

Compounds of formula (II) may he prepared by reacting a n acid of formula (IV), as defined above, with an amine of formula (X)

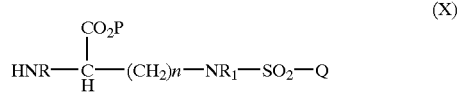

wherein P, including the carboxy group to which it is attached, is a suitable protecting group such as an alkoxy ester, for example ethoxycarbony; in an analogous method as described in process method (b) above, and subsequently conversion to the acid compound of formula (II) by deesterification.

Compounds of formula (IV) may be prepared by coupling of the B ring to the A ring as described in alternative process steps (d) and (f). For a coupling of A to B, via an alkyl bond, one ring is activated and the other contains a suitable displaceable group. Ideally the reaction is catalysed, such as with a palladium catalyst. Suitable reagents and conditions are described in a review article Harvey R. G. Organic Preparations and Procedures International, Vol. 29, (1997), 139.

Activated derivatives of heterocyclic ring A or B include metalised derivatives, such as with zinc or tin, borane derivatives and stannyl derivatives. Formation of the activated form desired is typically by substitution reactions. The activating group is added to the ring in place of a suitable leaving group or atom, such as halo or triflate. Suitable reagents and conditions are described in Shikara M. et.al.; Chem. Pharm. Bull.; 33(11), 4755–4763 (1985); Sandosham J. et.al.; Hetrerocycles, Vol. 37, No. 1, p501, (1994); and Salamoto T. et.al.; Tetrahedron: Vol. 49, No. 43, 9713–9720, (1993).

Alternatively compounds of formula (IV) may be prepared as described in process variant (e) above by forming A ring on the B ring containing a suitable functional group for cyclisaton. Suitable reagents and conditions are described in Bredereck H. Chem. Ber.; 96, 1505, (1963); Fuchigami. T., Bull. Chem. Soc. Jpn. 49, p3607, (1976); Huffman. K. R., J. Org. Chem., 28, p1812, (1963); Palusso G., Gazz, Chim. Ital., 90, p1290, (1960) and Ainsworth C. J., Heterocycl. Chem., 3, p470, (1966). Processes suitable for synthesis of starting materials in such cyclisation reactions are described in Zhang M. Q. et.al; J. Heterocyclic. Chem.; 28, 673, (1991 ) and Kosugi. M, et. al., Bull. Chem. Soc. Jpn., 60, 767–768 (1987).

Compounds of formula (XII) may be prepared via ring formation, such as described in Church R, et.al.: J. Org.

Chem., 60, 3750–3758, (1995) and Falck-Penderson M. L. et.al.; Acta Chem. Scand., 47, 63–67, (1993). Compounds formed by such reactions are also suitable starting materials for preparation of activated derivatives of the heterocyclic ring A by substitution reaction, as described above.

Compounds of formula (V) may be prepared by reacting an acid of formula (XI)

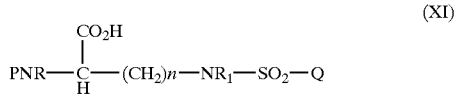

(XI)

wherein P is a protecting group, with an amine of formula (III), as defined above, in an analogous manner as described in method (a) above, and subsequently removing the protecting group.

Compounds of formula (VI) may be prepared from the amino acid of formula (XII)

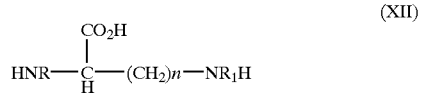

(XII)

by performing both reactions (a) and (b) described above, in either order, with the use of suitable protecting groups as described above.

Compounds of formula (VII) may be prepared by conversion of the thio analogue of the compound of formula (XIII), wherein Z is a dispaceable group

(XIII)

to the sulphonic acid halide by reactions as described in Kharasch N. Et.al.; J. Am. Chem. Soc., 73, p3240, 1951. Suitable reactions for the preparation of the thio analogues of compounds of formula (VII) are described in Newman M. S. et.al.; Organic synthesis. Vol. 51, p139.

Compounds of formula (VIII) may be prepared from compounds of formula (XI), as defined above, by performing reaction (a) described above and reacting the product with an acid of formula

Z—B—COOH (XIV)

in conditions similar to those described for reaction (b) above.

Compounds of formula (IX) may be prepared by an analagous reaction for the preparation of compounds of formula I using, method (c) above, reacting, a compound of formula (VI), as defined above, with a compound of formula (XIII), as defined above.

When a pharmaceutically-acceptable salt of compound of the formula I is required, it may be obtained, for example, by reaction of said compound with a suitable acid or base using a conventional procedure.

When an optically active form of a compound of the formula I is required, it may be obtained, for example, by carrying out one of the aforesaid procedures using an optically active starting material or by resolution of a racemic form of said compound using a conventional procedure.

As stated previously, the compounds of the formula I are inhibitors of the enzyme Factor Xa. The effects of this inhibition may be demonstrated using one or more of the standard procedures set out hereinafter:

a) Measurement of Factor Xa Inhibition

An in vitro assay system is carried out based on the method of Kettner et al., J. Biol. Chem., 1990, 265, 18289–18297, whereby various concentrations of a test compound are dissolved in a pI7.5 buffer containing 0.5% of a polyethylene glycol (PEG 6000) and incubated at 37° C. with human Factor Xa (0.001 Units/ml. 0.3 ml) for 15 minutes. The chromogenic substrate S-2765 (KabiVitrum AB, 2 $\mu$M) is added and the mixture is incubated at 37° C. for 20 minutes whilst the absorbance at 405 lime is measured. The maximum reaction velocity (Vmax) is determined and compared with that of a control sample containing no test compound. Inhibitor potency is expressed as an $IC_{50}$ value.

b) Measurement of Thrombin Inhibition

The procedure of method a) is repeated except that human thrombin (0.005 Units/ml) and the chromogenic substrate S-2238 (KabiVitrum AB, 7 $\mu$M) are employed.

c) Measurement of Anticoagulant Activity

An in vitro assay whereby human, rat or rabbit venous blood is collected and added directly to a sodium citrate solution (3.2 g/100 ml. 9 parts blood to 1 part citrate solution). Blood plasma is prepared by centrifugation (1000 g, 15 minutes) and stored at 2–4° C. Conventional prothrombin time (PT) tests are carried out in the presence of various concentrations of a test compound and the concentration of test compound required to double the clotting time, hereinafter referred to as CT2, is determined. In the PT test, the test compound and blood plasma are incubated at 37° C. for 10 minutes. Tissue thromboplastin with calcium (Sigma Limited, Poole, England) is added and fibrin formation and the time required for a clot to form are determined.

(d) Rat Disseminiated Intravascular Coagulation in vivo Activity Test

Fasted male Alderley Park rats (300–450 g) are pre-dosed by oral gavage (5 mls/kg) with compound or vehicle (5% DMSO/PEG200) at various times before being anaesthetised with Initraval® (120 mg/kg i.p.). The left jugular vein and the right carotid artery are exposed and cannulated. A 1 mL blood sample is taken from the carotid canular into 3.2% trisodium citrate, 0.5 mL of the whole blood is then treated with EDTA and used for platelet count determination whilst the remainder is centrifuged (5 mins, 20000 g) and the resultant plasma frozen for subsequent drug level, fibrinogen or thrombin antithrombin (TAT) complex determinations. Recombinant human tissue factor (Dade Innovin Cat.B4212-50), reconstituted to the manufacturers specification, is infused (2 mL/kg/hr) into the venous canular for 60 minutes. Immediately after the infusion is stopped a 2 mL blood sample is taken and platelet count, drug level, plasma fibrinogen concentration and TAT complex are determined as before. Platelet counting is performed using a Coulter T540 blood analyser. Plasma fibrinogen and TAT levels are determining using a clotting assay (Sigma Cat.880-B) and TAT ELISA (Behring) respectively. The plasma concentration of the compound is bioassayed using human Factor Xa and a chromogenic substrate S2765 (Kabi), extrapolated from a standard curve (Fragmin) and expressed in Anti-Factor Xa units. The data is analysed as follows: tissue factor-induced reductions in platelet count are normalised with respect to pre-dose platelet count and drug activity expressed as a percent inhibition of tissue factor-induced thrombocytopenia when compared to vehicle treated animals. Compounds are active if there is statistically significant ($p<0.05$) inhibition of TF-induced thrombocytopenia.

e) An ex vivo Assay of Anticoagulant Activity

The test compound is administered intravenously or orally to a group of Alderley Park Wistar rats. At various times thereafter animals are anaesthetised, blood is collected and PT coagulation assays analogous to those described hereinbefore are conducted.

According to a further feature of the invention there is provided a pharmaceutical composition which comprises a heterocyclic derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops: for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous. intramuscular, intravascular or infusion), for example a sterile aqueous or oily solution or suspension. In general the above compositions may be prepared in a conventional manner using, conventional excipients.

The amount of active ingredient (that is a heterocyclic derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of formula I, or a pharmaceutically acceptable salt thereof, for use in medical therapy.

According to a further feature of the invention there is provided a heterocyclic derivative of formula I, or a pharmaceutically-acceptable salt thereof, for use in a method of treatment of the human or animal body by therapy.

The invention also includes the use of such an active ingredient in the production of a medicament for use in:

(i) producing a Factor Xa inhibitory effect;
(ii) producing an anticoagulant effect;
(iii) producing an antithrombotic effect;
(iv) treating a Factor Xa mediated disease or medical condition;
(v) treating a thrombosis mediated disease or medical condition;
(vi) treating coagulation disorders: and/or
(vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula I will naturally vary according to the nature and severity of the medical condition the age and sex of the animal or patient being treated and the route of administration, according to well known principles of medicine. As mentioned above, compounds of the formula I are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed. for example a dose for intravenous administration in the range, for example, 0.5 to 50 mg/kg body weight will generally be used. For preferred and especially preferred compounds of the invention, in general, lower doses will he employed, for example a daily dose in the range, for example, 0.5 to 10 mg/kg body weight.

Although the compounds of the formula I are primarily of value as therapeutic or prophylactic agents for use in warm-blooded animals including man, they are also useful whenever it is required to produce an anticoagulant effect, for example during the ex-vivo storage of whole blood or in the development of biological tests for compounds leaving anticoagulant properties.

The compounds of the invention may be administered its a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

EXAMPLE 1

1-(1,1-Dioxothiomorpholino-4-carbonyl)-1-[1-(4-pyridyl)piperazin-4-ylcarbamoyl]-2-(bromonaphth-2-ylsulphonamido)ethane Method 1

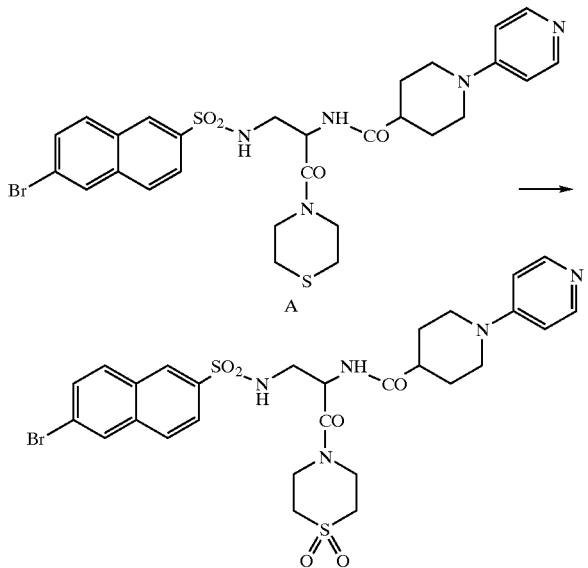

To a stirred suspension of A, prepared as in Example 2, (1.00 g, 1.548 mmole) in chloroform (50 ml) at room temperature was added metachloroperbenzoic acid (1.597 g, 4.644 mmole, 3 equivalents). A yellow gum formed. This gum was washed with dichloromethane (150 ml) and then with water (100 ml). The resulting yellow solid was triturated with ether and was dried in vacuo to give a pale yellow solid. This material was chromatographed on an alumina bond elute column, eluting with dichloromethane with increasing concentrations of methanol from 0% to 5%. The required product was eluted with 2% to 3% methanol in dichloromethane. Evaporation of these fractions yielded the product as a colourless solid (0.30 g, 28%).

NMR (300 MHz, DMSO) 1.4–1.6(m,2H): 1.6–1.7(m,2); 2.3–2.4(m,1H); 2.7–2.8(m,2H); 2.9–3.3(m,5H); 3.7–4.0(m, 6H); 4.7–4.9(m,1H); 6.7–6.8(m,2H); 7.7–7.9(m,3H); 8.0–8.2(m,5H); 8.3(s,1H); 8.5(s,1H); MS ES– (mH)+ 678.

Method 2

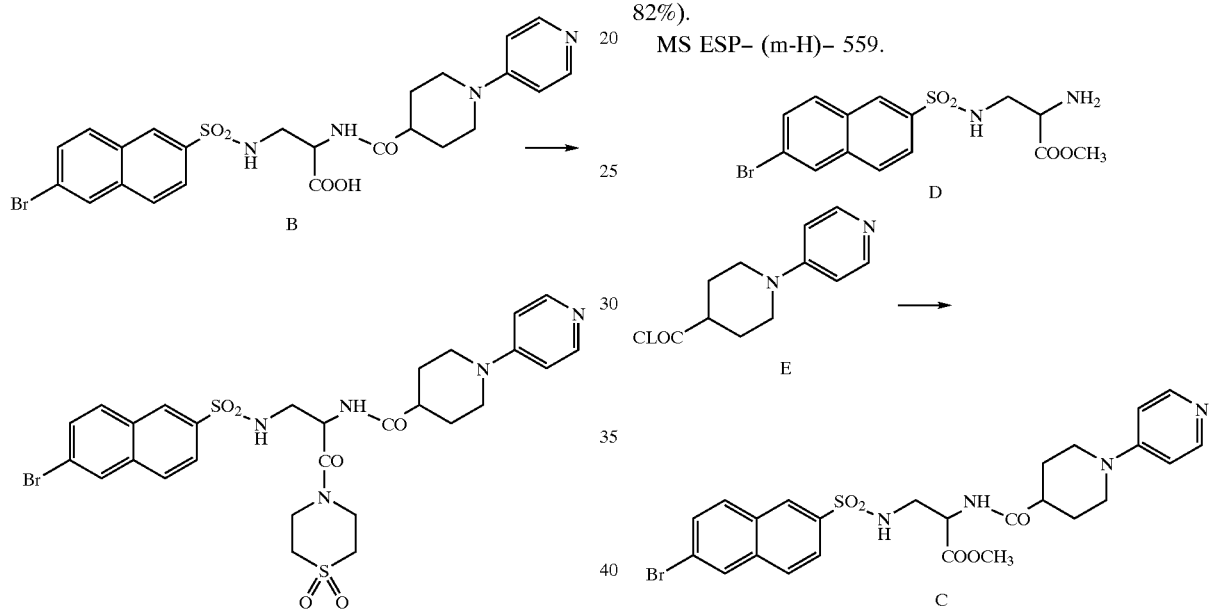

EDAC (10.283 g, 53.6 mmole) was added to a solution of B (35 g, 44.7 mmole), thiomorpholine sulphone trifluoroacetate (13.36 g, 53.6 mmole), n-hydroxybenztriazole (9.052 g, 67 mmole) and triethylamine(6.94 ml) in DMF (500 ml). Stirring was continued overnight. The mixture was poured into water (3.5 litres) and basified to pH8 with aqueous sodium hydroxide (2M). A white solid precipitated which was filtered off. The solid was dissolved in a mixture of dichloromethane and methanol (1:1 by volume). The resulting solution was boiled on the steam bath to reduce the volume until the solution became slightly cloudy. On cooling the required product separated as colourless crystals. The product was filtered off, washed with ether and dried.

The starting materials were prepared as follows;

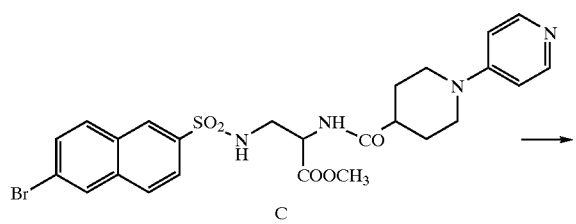

-continued

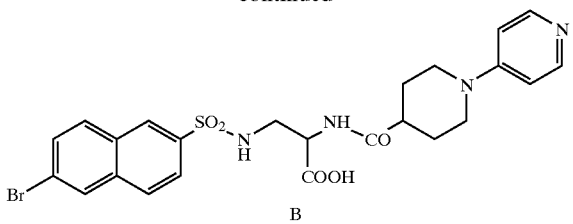

Sodium hydroxide (1M, 38.7 ml, 38.7 mmole) was added to a stirred solution of C (7.42 g, 12.9 mmole) in methanol (77 ml). After 1 hour the resulting solution was warmed and boiled under reflux for 0.75 hour, and then was allowed to cool to room temperature and stirred for a further 1 hour. The solution was acidified with 2M hydrochloric acid, and was evaporated in vacuo to yield B as a colourless solid (8.83 g, 82%).

MS ESP– (m-H)– 559.

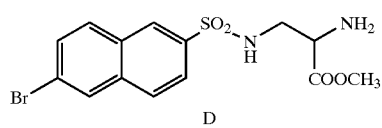

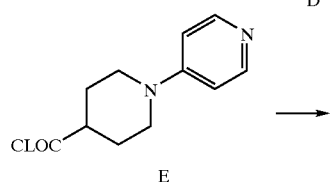

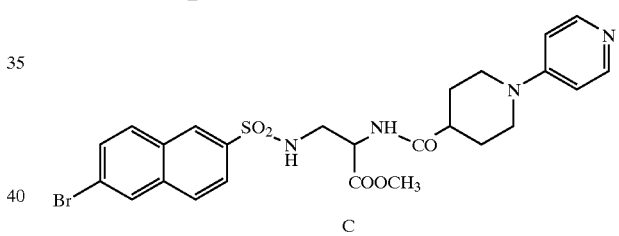

Thionyl chloride (10.54 ml, 144.6 mmole) was added to a stirred suspension of N-(4-pyridyl)piperidine-4-carboxylic acid (3.7245 g, 18.08 mmole) in dichloromethane (50 ml). Stirring was continued for 2 hours. The solvent was evaporated in vacuo and the residue re-evaporated from dichloromethane (3×50 ml) to leave the product E. A solution of this acid chloride in dichloromethane (50 ml) was added slowly to a stirred solution D chloride (7.0 g, 18.08 mmole) and triethylamine (7.546 ml, 54.2 mmole) in dichloromethane, and the resulting mixture was stirred overnight. The solution was poured into water (500 ml) and the resulting mixture was extracted with dichloromethane (3×100 ml). The combined extracts were dried over magnesium sulphate and evaporated to leave a yellow oil, This was chromatographed on a column of deactivated alumina (100 g), eluing with dichloromethane containing 1%, 2% and finally 3% methanol by volume. The fractions containing the required product C were evaporated in vacuo to afford a pale yellow foam (7.42 g, 71%).

NMR (300 MHz,DMSO) 14–15(m,2H); 1.6–1.7(m,2H); 2.3–2.4(m,1H); 2.7–2.9(m,2H); 3.1–3.2(m,2H); 3.55(s,3H); 3.8–3.9(m,2H); 4.3–4.4(m,1H); 6.75(d,2H); 7.75–7.85(m, 2H); 7.9–8.0(m,1H); 8.1–8.2(m,5H); 8.35(s,1H); 8.45(s, 1H). MS ESP+ (mH)+ 575.

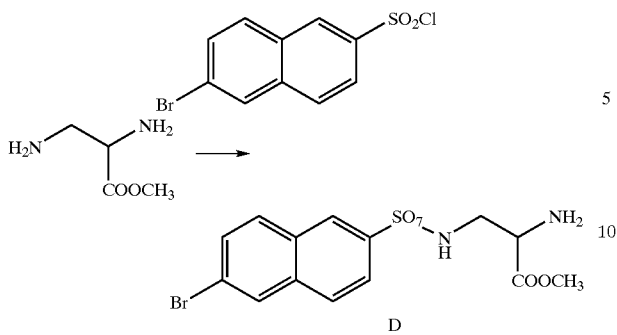

A solution of 6-bromonaphthalene-2-sulphonyl chloride (19.17 g, 71 mmole) in dichloromethane (150 ml) was added over 0.5 hour to a stirred mixture of methyl 2,3-diaminiopropionate dihydrochloride (13.561 g, 71 mmole) and triethylamine 29.63 ml, 213 mmoles) in dichloromethane (400 ml) at 0C. The solid gradually dissolved. The mixture was stirred at 0° C. for 1 hour and overnight at room temperature. The yellow solution was washed with water (2×350 ml). The combined extracts were dried over magnesium sulphate, and the solvent evaporated in vacuo to leave a brown residue. This was dissolved in methanol (500 ml) and hydrogen chloride in ether (1100 ml, 1M) was added. The solution was stirred for 1 hour, and was then evaporated in vacuo to leave a brown solid. Ethyl acetate (300 ml) was added and the mixture warmed to reflux. The brown solid changed in appearance to a colourless solid. The suspension was cooled and stirred at 0° C. for 10 minutes. The required product D was filtered off (16.26 g, 54%).

NMR (300 MHz., DMSO) 3.2–3.3(m,2H); 3.7(s,3H); 4.1(t,1H); 7.8(dd,1H); 7.9(dd,1H); 8.15(d,2H); 8.35(s,1H); 8.5(s,1H); 8.6–8.8(m,3H). MS ESP+ (mnH)+ 387.

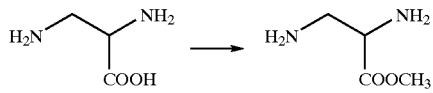

Thionyl chloride (22 ml) was added over 10 minutes to methanol (36 ml) at −5° C. with stirring. After stirring for a further 5 minutes at −5° C., 2,3-diaminopropionic acid monohydrochloride (10 g, 71 mmole) was added. The mixture was stirred at −5° C. for 3 hours, at which time all of the solid had dissolved. After stirring at room temperature for 2 hours, the solution was boiled under reflux for 1.5 hours, and was stood at room temperature overnight. Evaporation of the solvent in vacuo afforded the required product as colourless crystals (13.561, 100%).

NMR (300 MHz., DMSO) 3.2–3.4(m,2H); 3.7(s,3H); 4.4(t,1H); 8.6–9.2(m,6H). MS ESP+ (mH)+ 119.

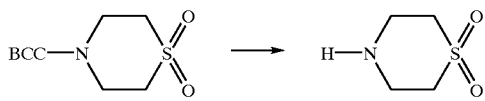

A solution of N-tert-butyloxycarbonyl thiomorpholine sulphone (14.805 g, 63 mmole) in trifluoroacetic acid (100 ml) was stirred at room temperature for 45 minutes. Evaporation of the solvent in vacuo afforded a yellow oil, which was dissolved in ether (500 ml). The required product separated as colourless crystals, which were filtered off, washed with ether (75 ml) and dried in vacuo. The yield was 17.55 g, 100%.

NMR (300 MHz, CDCl3) 3.4–3.5(m,4H); 3.5–3.6(m,4H).

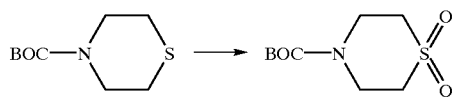

A solution of metachlorobenzoic acid (55%, 21.7 g) in chroroform (100 ml) and dichloromethane (100 ml) was added gradually over 40 minutes to a stirred solution of N-tert-butyloxycarbonyl thiomorpholine (6.4 g, 31.5 mmole) in chloroform (500 ml) kept below 20° C. The cooling bath was removed and the mixture was stirred at room temperature for 1 hour. The mixture was washed with aqueous sodium hydroxide(2M, 2×300 ml) and water (300 ml). The organic solution was dried over magnesium sulphate and the solvent evaporated in vacuo to yield the required product as a colourless solid (7.50 g, 100%).

NMR (300 MHz,CDCl3) 1.5(s,9H); 2.9–3.1(m,4H); 3.8–4.0(m,4H).

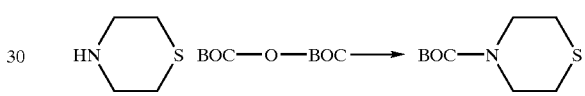

A solution of BOC—O—BOC (28.34 g, 0.13 Mole) in dichloromethane (100 ml) was added over 15 minutes to a solution thiomorpholine (13.05 ml, 0.13 Mole) and triethylamine (20.87 ml, 0.15 Mole) in dichloromethane (600 ml). The mixture was stirred for 1 hour. Vigorous evolution of carbon dioxide occurred. Ether (600 ml) was added and the organic solution was washed with citric acid (3×300 ml 1M), water (3×300 ml), brine (300 ml), dried over magnesium sulphate, and evaporated in vacuo to give N-tert-butyloxycarbonyl thiomorpholine as a colourless solid (26.5 g, 100%).

NMR (300 MHz,CDCl3) 1.4(s,9H); 2.5–2.6(m,4H); 3.6–3.65(m,4H). MS ESP+ (mH)+ 204.

EXAMPLE 2

1-(Thiomorpholino-4-carbonyl)-1-[1-(4-pyridyl) piperidine-4-ylcarbamoyl]-2-(bromonaphth-2-ylsulphonamido)ethane

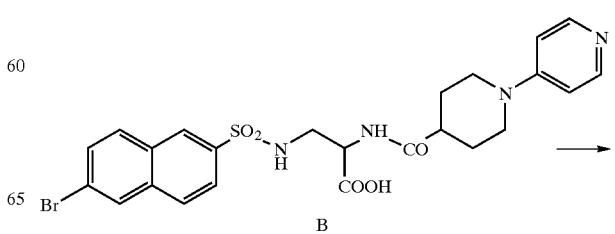

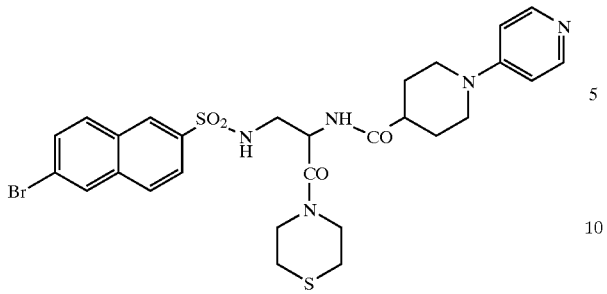

To a stirred solution of B (2.5 g, 3.652 mmole), thiomorpholine (0.442 ml, 4.38 mmole) and N-hydroybenztriazole (0.7395 g, 5.478 mmole) in DMT (20 ml) was added EDAC (0.840 g, 4.38 mmole). The solution was stirred overnight, and was then was poured into water (300 ml). This aqueous solution was adjusted to pH 12 by the addition of aqueous sodium hydroxide, and extracted with ethyl acetate (3×200 ml). The combined organic extracts were washed with water (300 ml), brine (100 ml), dried with magnesium sulphate, and the solvent evaporated to yield the required product as a pale yellow solid (2.21 g, 94%).

NMR (300 MHz, DMSO) 1,4–1.5(m,2H); 1.6–1.7(m, 2H); 2.3–2.5(m,2H); 2.7–2.9(m,3H); 3.0–3.1(m,1H); 3.6–3.9(m,8H); 4.7–4.8(m,1H); 6.75(d,2H); 7.8(d,1H); 7.85 (d,1H); 8.1–8.2(m,5H); 8.3(s,1H); 8.5(s,1H). MS ESP+ (mH)+ 646.

EXAMPLE 3

Using similar procedures as described in Example 2 the following were prepared, but starting with piperidine and morpholine respectively in place of thiomorpholine.

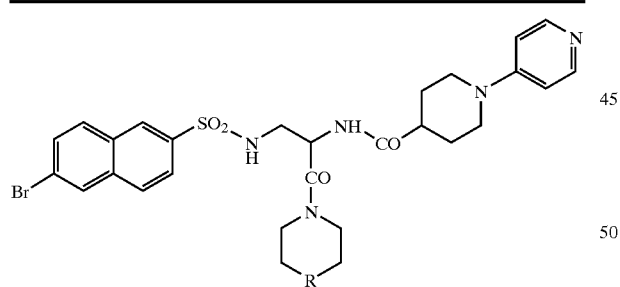

| No | R | NMR (300 MHz, DMSO) |
|---|---|---|
| 1 | $CH_2$ | 1.3–1.7 (m, 10H); 2.3–2.45 (m, 1H); 2.7–2.95 (m, 3H); 3.0–3.1 (m, 1H); 3.2–3.5 (m, 4H); 3.8–3.9 (m, 2H); 4.7–4.85 (m, 1H); 6.7–6.8 (m, 2H); 7.7–7.9 (m, 4H); 8.0–8.2 (m, 4H); 8.3 (s, 1H); 8.45 (s, 1H) MS ESP + (mH) + 628 |
| 2 | O | 1.4–1.5 (m, 2H); 1.6–1.7 (m, 2H); 2.3–2.4 (m, 1H); 2.5–3.0 (m, 4H); 3.0–3.1 (m, 1H); 3.2–3.6 (m, 7H); 3.8–3.9 (m, 2H); 4.7–4.8 (m, 1H); 6.7–6.8 (m, 2H); 7.7–7.9 (m, 3H); 8.0–8.2 (m, 5H); 8.3 (s, 1H); 8.5 (s, 1H) MS ESP + (mH) + 630 |

What is claimed is:

1. A compound of formula I, or a pharmaceutically-acceptable salt thereof,

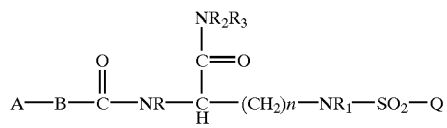

wherein:

A is a 5- or 6-membered monocyclic aromatic ring containing 1, 2 or 3 ring heteroatoms selected from oxygen, nitrogen and sulphur wherein A may be optionally substituted by one, two or three atoms or groups selected from halo, oxo, carboxy, trifluoromethyl, cyano, amino, hydroxy, nitro, (1–4C)alkyl, (1–4C)alkoxy, (1–4C)alkoxycarbonyl and, (1–4C)alkylamino or di-(1–4C)alkylamino;

B is a phenylene or a 6-membered heterocyclic ring containing 1, 2 or 3 nitrogen heteroatoms wherein B may be optionally substituted by halo, (1–4C)alkyl, (1–4C)alkoxy, (1–4C)alkylaminoethylamino, di-(1–4C)alkylamino, (2–4C)alkenyl, (2–4C)alkynyl, (2–4C)alkenyloxy, (2–4C)alkynyloxy, 4-(1–4C)alkylpiperazin-1-yl, (1–4C)alkylthio, (1–4C)alkylsulphinyl, (1–4C)alkylsulphonyl, (2–4C)alkanoylamino, (1–4C)alkanesulphonamido, (1–4C)alkoxycarbonyl, N-(1–4C)alkylcarbamoyl, N,N-di-[(1–4C)alkyl]carbamoyl, 4-(1–4C)alkylpiperazin-1-ylcarbonyl, (1–4C)alkanesulphonamidocarbonyl, (2–4C)alkanoyl, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, or N,N-di-[(1–4C)alkyl]carbamoyl-(1–4C)alkyl;

R and $R_1$ are independently selected from hydrogen and (1–4C)alkyl;

n is 1 or 2;

$R_2$ and $R_3$, in combination with the nitrogen to which they are attached, form a 6-membered heterocyclic ring which may have in addition to the nitrogen atom 1 or 2 heteroatoms selected from nitrogen, oxygen and sulphur, wherein the heterocyclic ring formed from $R_2$ and $R_3$ may be optionally substituted by hydroxy, amino, carboxy, (1–4C)alkoxycarbonyl, oxo, (1–4C)alkyl, hydroxy-(1–4C)alkyl, (1–4C)alkoxy-(1–4C)alkyl, carboxy-(1–4C)alkyl, (1–4C)alkoxycarbonyl-(1–4C)alkyl, or carbamoyl-(1–4C)alkyl; and Q is selected from phenyl, naphthyl, phenyl(1–4C)alkyl, phenyl(2–4C)alkenyl and a 5-, 6- or 7-membered heterocyclic ring containing up to 4 heteroatoms selected from nitrogen, oxygen and sulphur wherein Q may be optionally substituted by halo, halo(1–4C)alkyl, cyano, amino, hydroxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di(1–4C)alkylamino, (1–4C)alkoxycarbonyl, N-(1–4C)alkylcarbonoyl, (2–6C)alkanoyl, (2–4C)alkanoylamino, hydroxy-(1–4C)alkyl, (1–4C)alkoxy-(1–4C)alkyl, carboxy-(1–4C)alkoxycarbonyl-(1–4C)alkyl, carbamoyl-(1–4C)alkyl, N-(1–4C)alkylcarbamoyl-(1–4C)alkyl, N,N-di(1–4C)alkylcarbamoyl-(1–4C)alkyl, phenyl, phenoxy, phenylthio, phenylsulphinyl, phenylsulphonyl, benzyl, or benzoyl, wherein said phenyl, phenoxy, phenylthio, phenylsulphinyl, phenylsulphonyl, benzyl or benzoyl substituent bears 1, 2 or 3 substituents selected from halo, trifluoromethyl, cyano, hydroxy, amino, nitro, carboxy, carbamoyl, (1–4C)alkyl, (1–4C)alkoxy, (1–4C)alkylamino, di(1–4C)alkylamino, (1–4C)alkoxycarbonyl, N,-(1–4C)alkylcarbomoyl, N,N,(1–4C)alkylcarbamoyl and (2–4C)alkenoylamino.

2. The compound of formula I as claimed in claim 1, wherein B is a 1,4-piperidinediyl or 1,4-piperazinediyl ring.

3. The compound of formula I as claimed in claim 1 or claim 2 wherein Q is naphthyl.

4. The compound of formula I as claimed in claim 3 wherein Q is substituted by halo or (1–4C)alkyl.

5. The compound of formula I as claimed in claim 1 or claim 2 wherein A is 4-pyrimidinyl or 4-pyridyl.

6. The compound of formula I as claimed in claim 5 wherein A is substituted by a substituent selected from halo, (1–4C)alkyl, amino and (1–4C)alkylamino.

7. A pharmaceutical composition comprising a compound of formula I, as defined in claim 1 or claim 2, and a pharmaceutically acceptable diluent or carrier.

8. A method for the treatment of a disease or medical condition mediated by Factor Xa comprising administering to a warm-blooded animal in need thereof a treatment-effective amount of a compound as defined in claim 1 or claim 2.

9. A method for the inhibition of Factor Xa in a warm-blooded animal in need thereof comprising administering to said animal a Factor Xa inhibiting amount of a compound as defined in claim 1 or claim 2.

10. A method for the treatment of cardiovascular or cerebrovascular disease in a warm-blooded animal in need thereof comprising administering to said animal a treatment-effective amount of a compound as defined in claim 1 or claim 2.

* * * * *

UNITED STATES PATENT AND TRADEMARK OFFICE
CERTIFICATE OF CORRECTION

PATENT NO. : 6,486,154 B1
DATED : November 26, 2002
INVENTOR(S) : Stocker et al.

It is certified that error appears in the above-identified patent and that said Letters Patent is hereby corrected as shown below:

Column 20,
Line 22, change "(1-4C)alkylaminoethylamino" to read -- (1-4C)alkylamino --
Lines 63-64, change "carboxy-(1-4C)alkoxycarbonyl-(1-4C)alkyl" to read -- carboxy-(1-4C)alkyl, (1-4C)alkoxycarbonyl-(1-4C)alkyl --.

Column 21,
Line 7, change "N,-(1-4C)alkylcarbomoyl" to read -- N,-(1-4C)alkylcarbamoyl --.

Signed and Sealed this

Sixth Day of May, 2003

JAMES E. ROGAN
*Director of the United States Patent and Trademark Office*